United States Patent [19]

Iwai

[11] Patent Number: 4,680,313

[45] Date of Patent: Jul. 14, 1987

[54] ACCELERATION OF LIPID METABOLISM USING VANILLYLAMINE DERIVATIVES

[75] Inventor: Kazuo Iwai, Kyoto, Japan

[73] Assignee: Ajinomoto Co., Inc., Tokyo, Japan

[21] Appl. No.: 834,102

[22] Filed: Feb. 24, 1986

Related U.S. Application Data

[63] Continuation of Ser. No. 742,317, Jun. 7, 1985, abandoned.

[30] Foreign Application Priority Data

Jun. 11, 1984 [JP] Japan ................................. 59-119460
Jun. 11, 1984 [JP] Japan ................................. 59-119461
Dec. 26, 1984 [JP] Japan ................................. 59-281691

[51] Int. Cl.$^4$ ...................... A61K 31/16; A61K 31/35
[52] U.S. Cl. .................................... 514/627; 514/625; 514/655; 514/909
[58] Field of Search ................ 514/625, 627, 909, 655

[56] References Cited

U.S. PATENT DOCUMENTS 3,728,459 4/1973 Seki et al. ............................ 514/627
4,532,139 7/1985 Janusz et al. ........................ 514/627

OTHER PUBLICATIONS

Chem. Abst. 81:99511z (1974)–Nopanitaya.
Chem. Abst. 90:21230y (1979)–Sambaiah et al.
Chem. Abst. 92:179628k (1980)–Srinivasan et al.
Chem. Abst. 93:166630(a) (1980)–Sambaiah et al.
Chem. Abst. 97:71327(a) (1982)–Ki et al.
Chem. Abst. 99:52372m (1983)–Sambaiah et al.
Fenaroli's–Handbook of Flavor Ingredients–2nd ed. (1975), vol. 2–p. 266–CRC Press–Cleveland, Ohio.

Primary Examiner—Douglas W. Robinson
Attorney, Agent, or Firm—Oblon, Fisher, Spivak, McClelland & Maier

[57] ABSTRACT

A food product comprising a food substance in combination with vanillylamine or a vanillylamide.

9 Claims, 9 Drawing Figures

4,680,313

ACCELERATION OF LIPID METABOLISM USING VANILLYLAMINE DERIVATIVES

This application is a Continuation of application Ser. No. 742,317, filed June 7, 1985, now abandoned.

BACKGROUND OF THE INVENTION

1. Field of the Invention

This invention relates to foods which contain vanillylamine or a vanillylamide (hereinafter collectively called vanillylamine derivatives) and therefore are effective in reducing or in preventing increases body fat.

2. Description of the Background

Obesity, which is caused by excessively high caloric intake and the resulting accumulation of surplus fat often leads to various types of geriatric diseases. Furthermore, the accumulation of body fat endangers the health of those people who are free to take in much fat and carbohydrate and whose physical constitution or conditions in daily living are not in favor of the metabolism of these nutrients. Dieting or sitotherapy is now a matter of major concern to patients who suffer from obesity-caused diseases and also to healthy people who need to control their weight.

Dieting or sitotherapy often requires limitations on the intake of fat and carbohydrate, and it can also restrict the total number of meals consumed as well as the caloric intake, as may be seen from the examples shown later. Thus, dieting is not always successful in achieving the desired objectives, because it requires the utmost in patience on the part of the dieter. Hence, a significant number of dieters fail to persist through their diets.

There has been a great demand for foods which will help reduce the amount of body fat without limiting the kinds and quantities of food consumed, and which do not lead the dieter to resort to the taking of medicines. Such foods, if available, would also be of great benefit to healthy people who wish to reduce surplus fat and maintain a normal body weight.

The means for reducing body fat and for preventing its accumulation may be classified into two types: (1) the reduction of caloric intake which is exemplified by the use of sweeteners of high sweetness and the intake of unmetabolizable foods such as konjak (glucomannan) jelly, and by the administration of anorexigenic agents; and (2) the promotion of fat metabolism, exemplified by physical methods such as gymnastic exercises and massages, and by the intake of foods or medicines that accelerate fat metabolism. A variety of medicines that promote the metabolism of body fat are known and they include lipid metabolism improvers such as nicotinic acid, dl-α-tocopherol, oxandrolone and clofibrate. On the other hand, foods having such a metabolic activity are very few. Some such health foods proposed in Japanes Patent Laid-Open No. 122,765 (1982) contain, as essential ingredients, the concentrate of saponin components extracted from a cucurbitaceous plant.

With respect to vanillylamine derivatives, capsaicin, which is a vanillylamide derived from a carboxylic acid of 10 carbon atoms, which is a typical pungent principle, is known to have anti-oxidant action [Japanese Patent Publication No. 40,876 (1976); Oil Chemistry, 29, No. 6, 31–34 (1980)]. However no other utility for the compounds of this family of compounds has yet been reported. A need therefore continues to exist for foods which promote the metabolism of fat.

SUMMARY OF THE INVENTION

Accordingly, one object of the present invention is to provide foods which help to reduce, or prevent the accumulation of, body fat, thereby reducing or maintaining body weight, for patients suffering hyperlipemia or other obesity-caused diseases and for those people who are trying to control body weight.

Briefly, this object and other objects of the present invention as hereinafter will become more readily apparent can be attained by adding to fat or no-fat containing foods (I) a vanillylamide derived from an unsaturated carboxylic acid of 9 to 11 carbon atoms, (II) vanillylamine, (III) a vanillylamide derived from a saturated carboxylic acid, or (IV) a vanillylamide derived from an unsaturated carboxylic acid having less than 9 or more than 11 carbon atoms.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

DETAILED DESCRIPTION OF THE PREFERRED EMBODIMENTS

Figure 1:
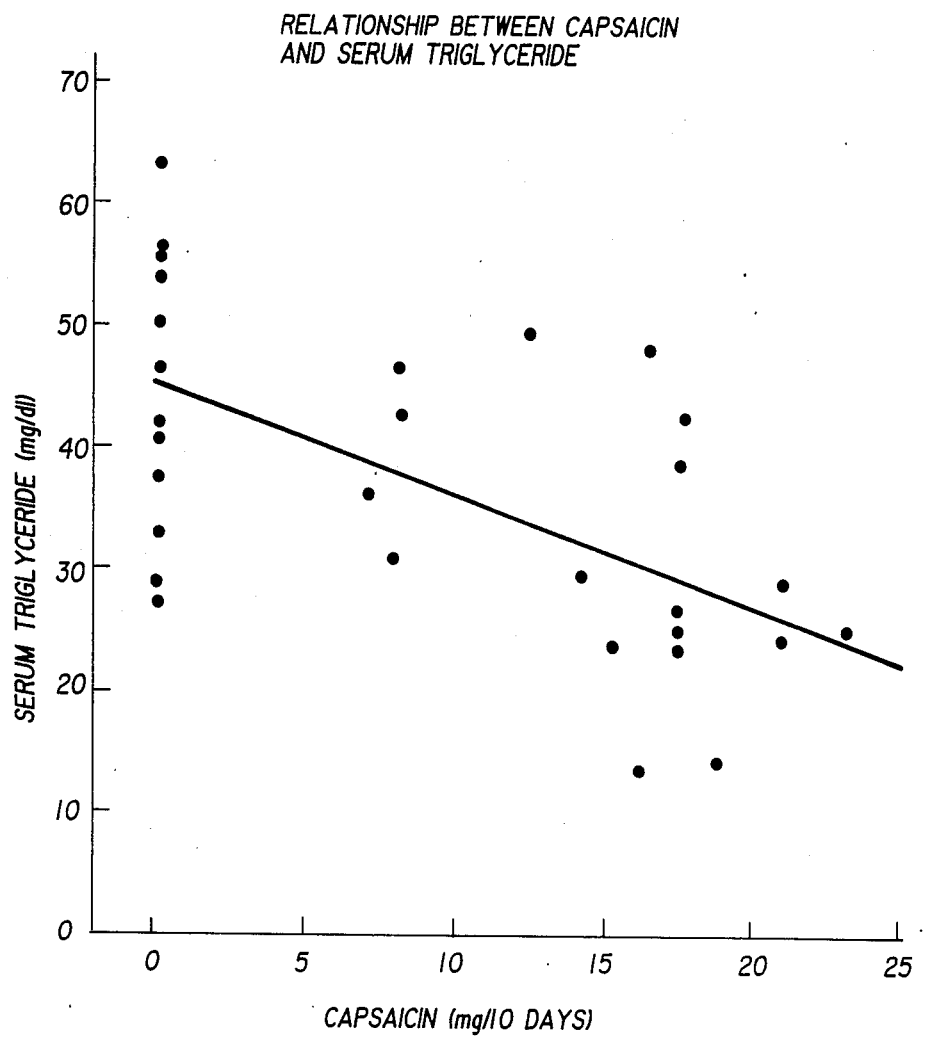
FIG. 1 shows the relationship between the amount of capsaicin (CAP) and the triglyceride level in blood.

Suitable examples of vanillylamides (I) derived from unsaturated carboxylic acids of 9 to 11 carbon atoms include capsaicin of formula (1), norcapsaicin of formula (2) and homocapsaicin of formula (3), all formulas shown below. In addition to these compounds, 2,6-octadienamide (4), 6-nonenamide (5), 10-undecenamide (6), 7-decenamide (7), and 6-decenamide (8) are also known. These and any other vanillylamides derived from unsaturated carboxylic acids of 9 to 11 carbon atoms, both natural and synthetic, may be used in the present invention.

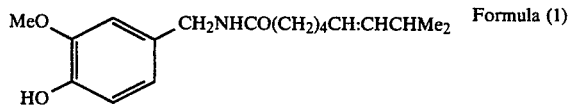

Formula (1)

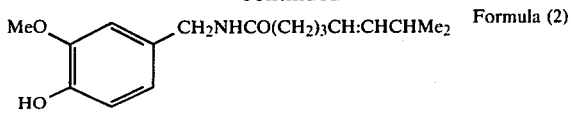 Formula (2)

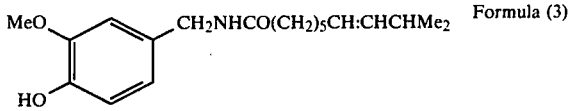 Formula (3)

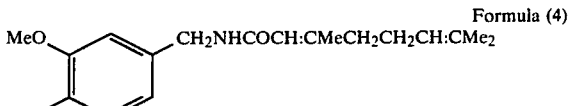 Formula (4)

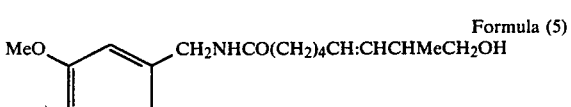 Formula (5)

 Formula (6)

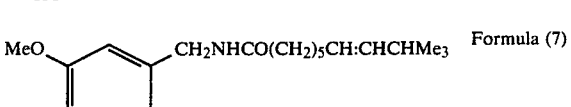 Formula (7)

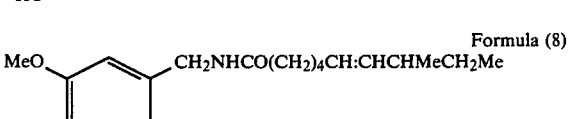 Formula (8)

Suitable examples of the vanillylamides derived from saturated carboxylic acids (III) include dihydrocapsaicin of formula (9), nordihydrocapsaicin of formula (10) and homodihydrocapsaicin of formula (11), all shown below. Besides these compound, nonanamides (12,13,14), propionamide (15), octanamides (16,17), decanamides (18,19), undecanamide (20), butanamide (21), acetamide (22), octadecanamide (23), hexanamide (24), heptanamide (25), dodecanamide (26), tetradecanamide (27), hexadecanamide (28), and docosanamide (29) are also known. These compounds and any other saturated vanillylamides, both natural and synthetic, may be used in the present invention.

 Formula (9)

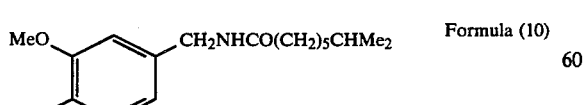 Formula (10)

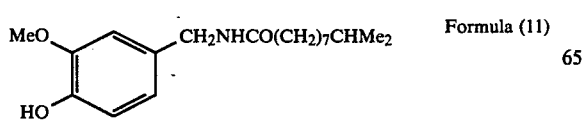 Formula (11)

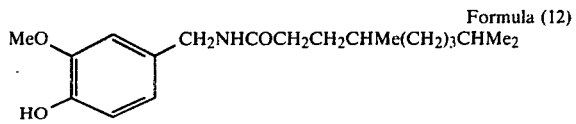 Formula (12)

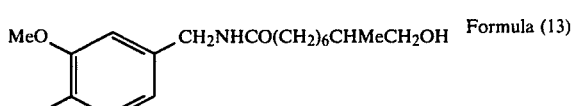 Formula (13)

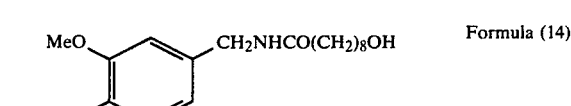 Formula (14)

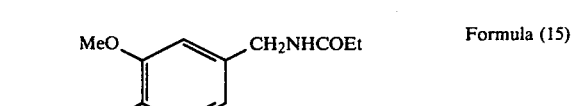 Formula (15)

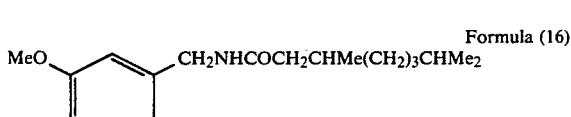 Formula (16)

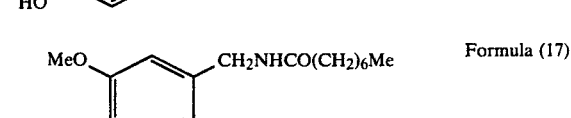 Formula (17)

 Formula (18)

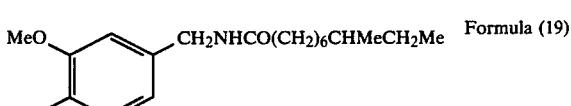 Formula (19)

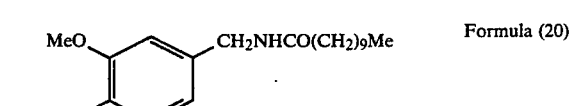 Formula (20)

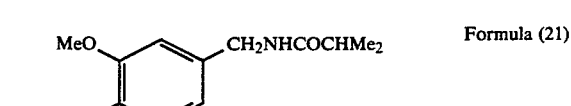 Formula (21)

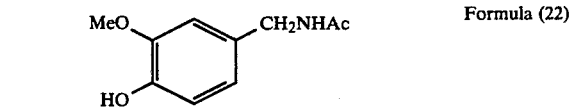 Formula (22)

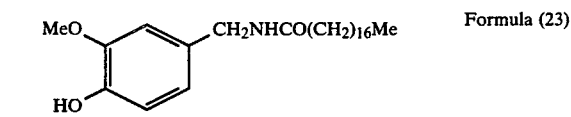 Formula (23)

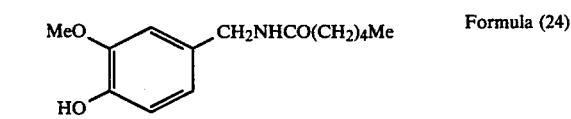 Formula (24)

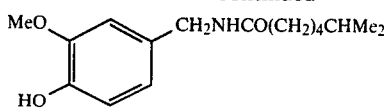 Formula (25)

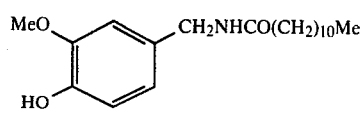 Formula (26)

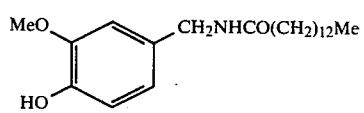 Formula (27)

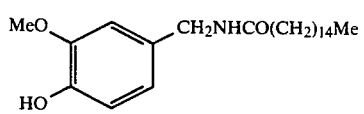 Formula (28)

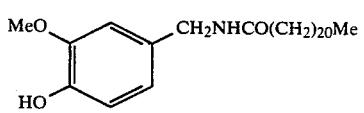 Formula (29)

Suitable examples of the vanillylamides derived from unsaturated carboxylic acids having less than 9 or more than 11 carbon atoms (IV) include bishomocapsaicin ($C_{20}H_{31}NO_3$) and tris-homocapsaicin ($C_{21}H_{33}NO_3$), as well as 4-heptenamide (30), linolamide (31) and 9-octadecenamide (32). These compounds and any other vanillylamides derived from unsaturated carboxylic acids having less than 9 or more than 11 carbon atoms, both natural and synthetic, may be used in the present invention.

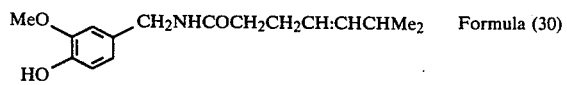 Formula (30)

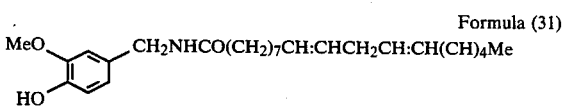 Formula (31)

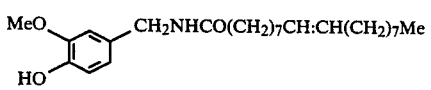

The vanillylamine derivatives of the invention may be used either alone or in combination. For example, plants containing vanillylamine derivatives may be incorporated in foods without any special treatment, or extracts therefrom may also be employed.

The larger the amount of vanillylamide derivative used, the greater will be the effect intended by the present invention. However, there is some limitation upon the content for some of the vanillylamide derivatives in a food substance. Vanillylamides derived from carboxylic acids of 9 to 11 carbon atoms, in particular, generally have a strongly pungent taste and may spoil, if added in a large quantity to food. The palatability of the resulting food substance depends on the type and proportion of the ingredients it contains. Hence, when a vanillylamide derived from a carboxylic acid of 9 to 11 carbon atoms is used, it is preferred that it be employed in combination with vanillylamine or a vanillylamide derived from a carboxylic acid containing less than 9 or more than 11 carbon atoms (in place of using a vanillylamide of 9 to 11 carbon atoms alone at high concentrations). When a vanillylamide of this type is to be employed alone, suitable expedients should be adopted so as to dull its pungent taste in the mouth. That is, encapsulation, the addition of acidulating, sweetening or other agents that moderate pungent taste, or dilution prior to intake. For food substances which are taken without being diluted, the content of a vanillylamide derived from a carboxylic acid of 9 to 11 carbon atoms should preferably be less than 1% to ensure palatability. However, it is possible to provide foods containing such vanillylamides at higher concentrations, if an expedient as mentioned above is employed such as encapsulation combined with other ingredients that moderate the pungent taste. There is no specific lower limit for the concentration of this type of vanillylamide, but the effect intended by this invention can hardly be expected if the concentration falls below 0.01%. Hence, a suitable concentration of vanillylamides derived from carboxylic acids of 9 to 11 carbon atoms lies in the range from 0.01% to 1%, more preferably from 0.1% to 1%. On the other hand, when vanillylamine or a vanillylamide derived from a carboxylic acid having less than 9 or more than 11 carbon atoms is used alone, no such sensory problem exists even at high concentrations.

The food substances of the present invention include edible fats and oils, and food products containing the same, where animal fats include the likes of butter, lard and beef fat; animal oils includes the likes of fish oil; and vegetable oils include the likes of rapeseed oil, soybean oil, cottonseed oil and corn oil. Other fats and oils include hardened vegetable oil, and vegetable fat. Other foods include processed foods containing fat and oil such as fried foods, Worcester sauce, mayonnaise, dressings, paste, sausages, ham, non-defatted fish, and meat, and food products containing no fat or oil such as oil-free seasoners, meat tenderizers and beverages including those which are taken with fatty foods. Any of these foods may be used as the base material to give a food product which is effective in reducing, or preventing increases in body fat, thereby reducing body weight or maintaining it at a normal level.

There is no specific method which must be used to combine the vanillylamine derivative with a food base. But when a vanillylamide derived from a carboxylic acid of 9 to 11 carbon atoms is combined at high concentrations with a food substance, i.e., more than 1% at intake, it is advisable to use a special processing technique, such as the encapsulation technique. Preferably, the vanillylamine derivative is sealed with a material that will remain stable in the mouth and decompose in the digestive tract.

Having generally described this invention, a further understanding can be obtained by reference to certain specific examples which are provided herein for purpose of illustration only and are not intended to be limiting unless otherwise specified.

The following basic experiments were conducted using diets containing capsaicin.

Effect of capsaicin upon lipid metabolism in rats fed on high-fat food

Experimental

Male Wister rats of an initial weight of 170 to 180 grams were divided into three groups, and each group was fed on high-fat diet A, high-fat diet B, or a commercial diet (Oriental Yeast Co., Ltd., Oriental MF Diet), respectively, for ten days. The compositions of high-fat diets A and B are given in Table 1 (fat energy ratio: 60%). The triglyceride level in the blood of each rat tested was measured, as well as the total weight of peri-renal adipose tissue, the activity of glucose-6-phosphate hydrogenase which participates in fatty acid synthesis in the liver, and the activity of lipoprotein lipase in the peri-renal adipose tissue.

TABLE 1

|  | High-fat Diet A | High-fat Diet B |
|---|---|---|
| Diet |  |  |
| Casein | 10% | 10% |
| Starch | 39.986 | 40 |
| Sucrose | 10 | 10 |
| Mixed minerals | 2 | 2 |
| Mixed vitamines | 1 | 1 |
| Cellulose | 2 | 2 |
| Capsaicin | 0.014 | — |
| Lard | 30 | 30 |
| Soybean oil | 5 | 5 |

TABLE 2

(Experimental Results)

|  |  | High-fat Diet A | High-fat Diet B | Commercial Diet (Control) |
|---|---|---|---|---|
| 1 | Caloric intake (cal/10 days) | 548.6 ± 4.9 | 547.2 ± 2.7* | 549.0 |
| 2 | Triglyceride level in blood (mg/dl) | 29.3 ± 13.0$^a$ | 41.7 ± 16.9$^b$ | 26.1 ± 5.6*$^a$ |
| 3 | Free fatty acids (mg/dl) | 6.45 ± 1.78 | 6.51 ± 1.21 | 6.30 ± 1.06 |
| 4 | Cholesterols (mg/dl) | 140.2 ± 22.0$^b$ | 140.3 ± 46.8$^b$ | 104.9 ± 10.9$^a$ |
| 5 | Weight of peri-renal adipose tissue (g) | 1.69 ± 0.50$^c$ | 2.23 ± 0.55$^b$ | 0.36 ± 0.24$^a$ |
| 6 | Fat absorption efficiency (%) | 98.9 ± 0.3 | 98.4 ± 0.2 | 99.6 ± 0.1 |
| 7 | Liver: glucose-6-phosphate hydrogenase activity (unit/g-liver) | 1.09 ± 0.17$^a$ | 0.76 ± 0.33$^b$ | 1.04 ± 0.20$^a$ |
| 8 | β-Hydroxyacyl-CoA dehydrogenase activity (m-unit/g-liver) | 53.5 ± 9.3$^a$ | 53.0 ± 5.7$^b$ | 39.7 ± 9.2$^a$ |
| 9 | Renal adipose tissue: hormone-sensitive lipase (free fatty acid μmol/μg-DNA/hr) | 4.45 ± 0.52$^b$ | 4.92 ± 0.55$^b$ | 3.22 ± 0.79$^b$ |
| 10 | Lipoprotein lipase (μmol/μg-DNA/hr) | 25.5 ± 2.2$^a$ | 20.5 ± 0.9$^b$ | 23.0 ± 4.4$^a$ |

*Standard deviation
$^{a,b,c}$Significant difference (95%) exists among a, b and c on the same lines.

As is apparent from Table 2, significant reduction in the weight of peri-renal adipose tissue and in the triglyceride level in blood was observed with the group of rats fed on high-fat diet A containing capsaicin, in comparison to the group fed on high-fat diet B with no capsaicin. Similarly, a significant increase was observed in the activity of lipoprotein lipase in the peri-renal tissue and in the activity of glucose-6-phosphate dehydrogenase which participates in biosynthesis of fatty acids in the liver with the diet A group. These results suggest that capsaicin-containing diets of this invention help promote lipid metabolism in rats fed on high-fat foods.

Figure 2:
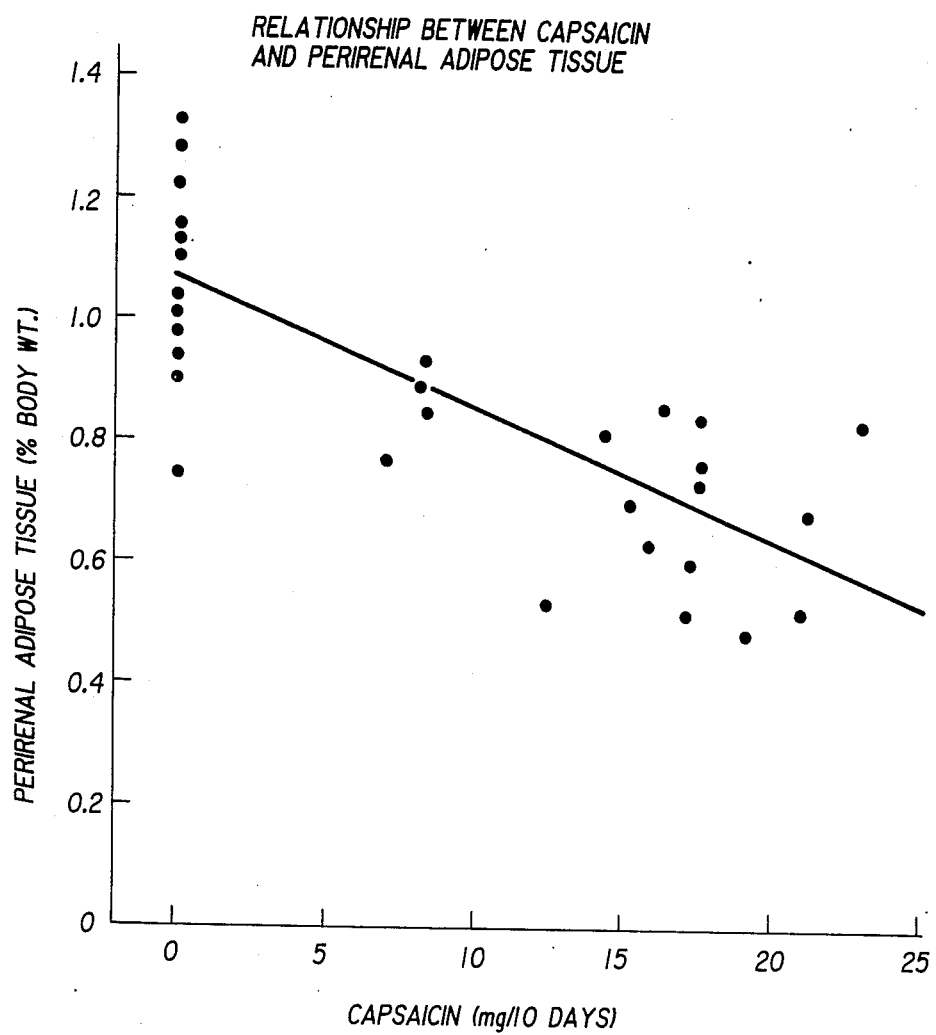
FIG. 2 shows the relationship between the amount of CAP and the weight of peri-renal adipose tissue.

Relationship between the amount of capsaicin added versus triglyceride level in blood and weight of peri-renal adipose tissue Male Wister rats of an initial weight of 170 to 180 grams were fed on high-fat diets A and B (the same composition as in Table 1, with only the amount of capsaicin being varied), and the triglyceride level in the blood and the weight of peri-renal adipose tissue were measured after ten days. The results are summarized in FIGS. 1 and 2, which clearly show that a negative correlation exists between the amount of capsaicin versus triglyceride level and adipose tissue weight.

Figure 3:
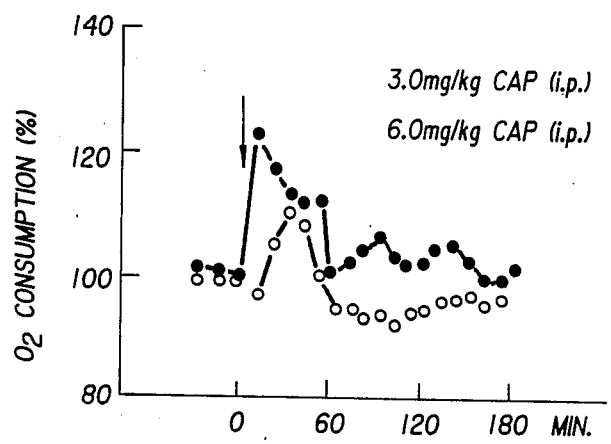
FIG. 3 shows the effect of CAP upon oxygen consumption.
Figure 4:
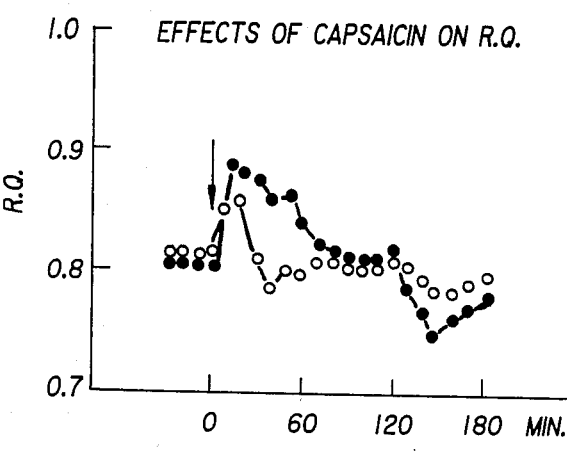
FIG. 4 shows the effect of CAP upon the respiratory quotient.
Figure 5:
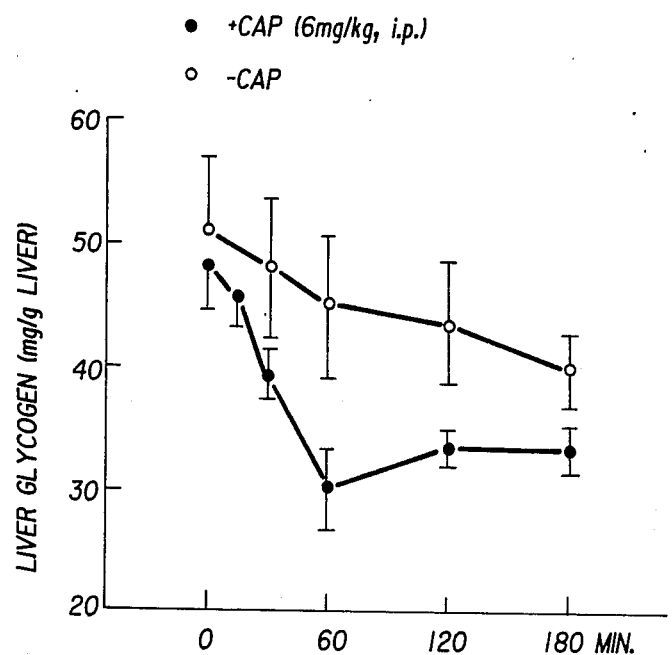
FIG. 5 shows the effect of CAP upon hepatic glycogen.
Figure 6:
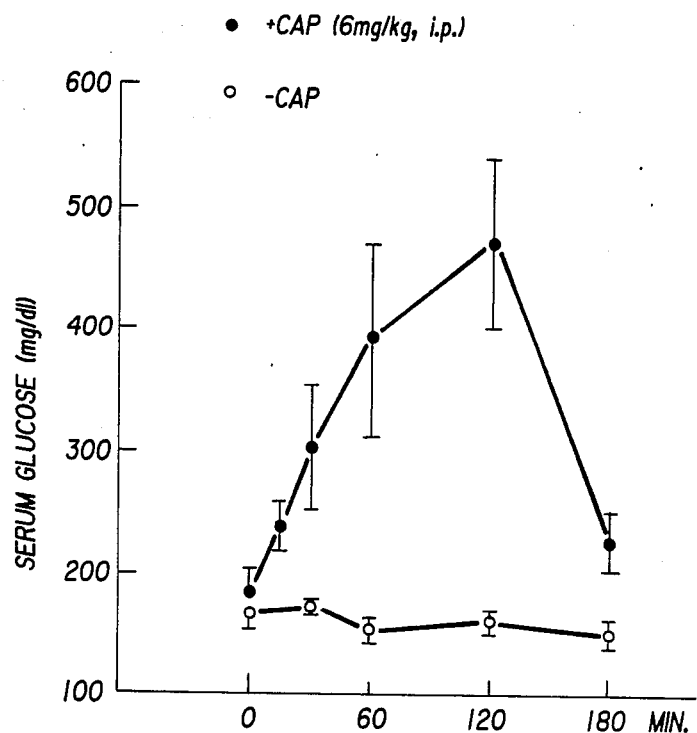
FIG. 6 shows the effect of CAP upon the glucose level in blood.
Figure 7:
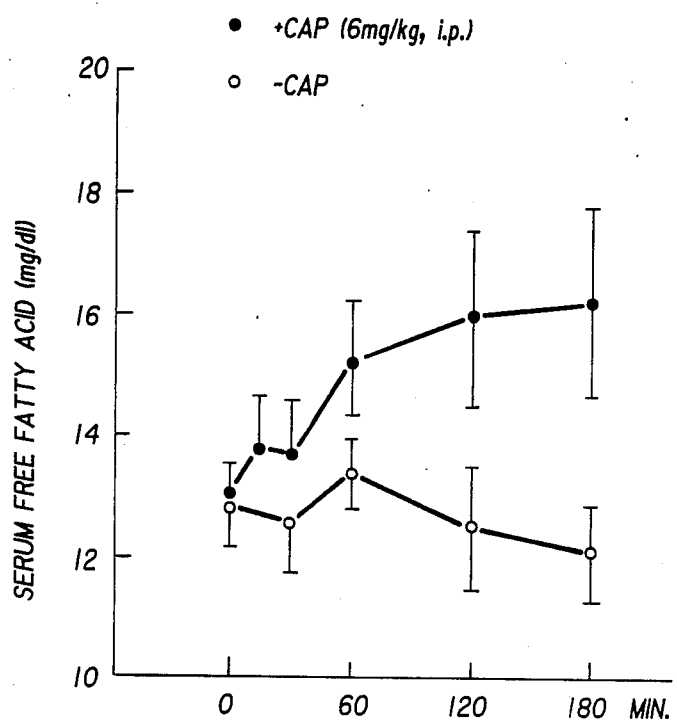
FIG. 7 shows the effect of CAP upon the free fatty acid level in blood.

In-vivo analysis on the lipid metabolism accelerating action of capsaicin in rats Changes in energy metabolism in rats caused by the consumption of capsaicin (oxygen consumption and respiratory quotient) were measured to characterize the mechanism of its lipid metabolism accelerating action (FIG. 3). Upon abdominal injection of capsaicin (6 mg/Kg) into rats, their oxygen consumption sharply increased, reaching a maximum in 20 to 30 minutes. The value then declined to the original level after one hour, but some actions caused by accelerated lipid metabolism were observed to continue for 60 to 150 minutes. The respiratory quotient also responded quickly to the injection of capsaicin, rising to about 0.89 in 10 to 30 minutes, and then falling to the original level (about 0.80) in 60 to 70 minutes. This level was maintained for an additional 60 minutes or so, then decreased again to reach a minimum (about 0.75) after 150 minutes, and finally increased to the original value after 180 minutes (FIG. 4). It was also demonstrated that the amount of hepatic glycogen continued to decrease after injection of capsaicin (FIG. 5), which was accompanied by an increase in the glucose level in the blood (FIG. 6) and an increase in the content of free fatty acids in the blood (FIG. 7).

Figure 8:
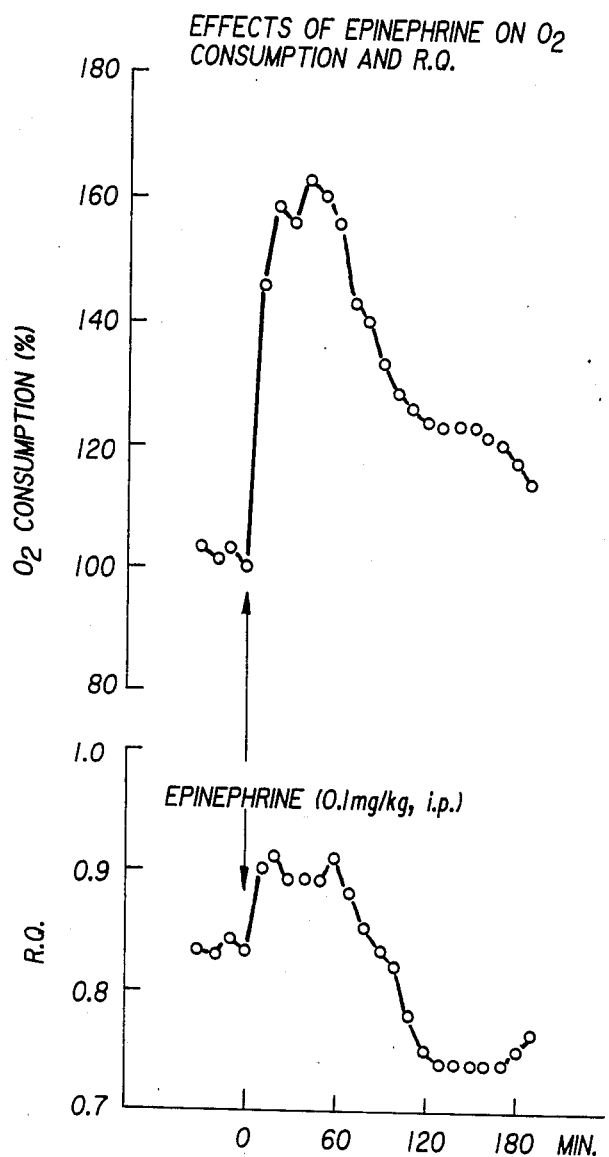
FIG. 8 shows the effect of epinephrine upon oxygen consumption and the respiratory quotient.
Figure 9:
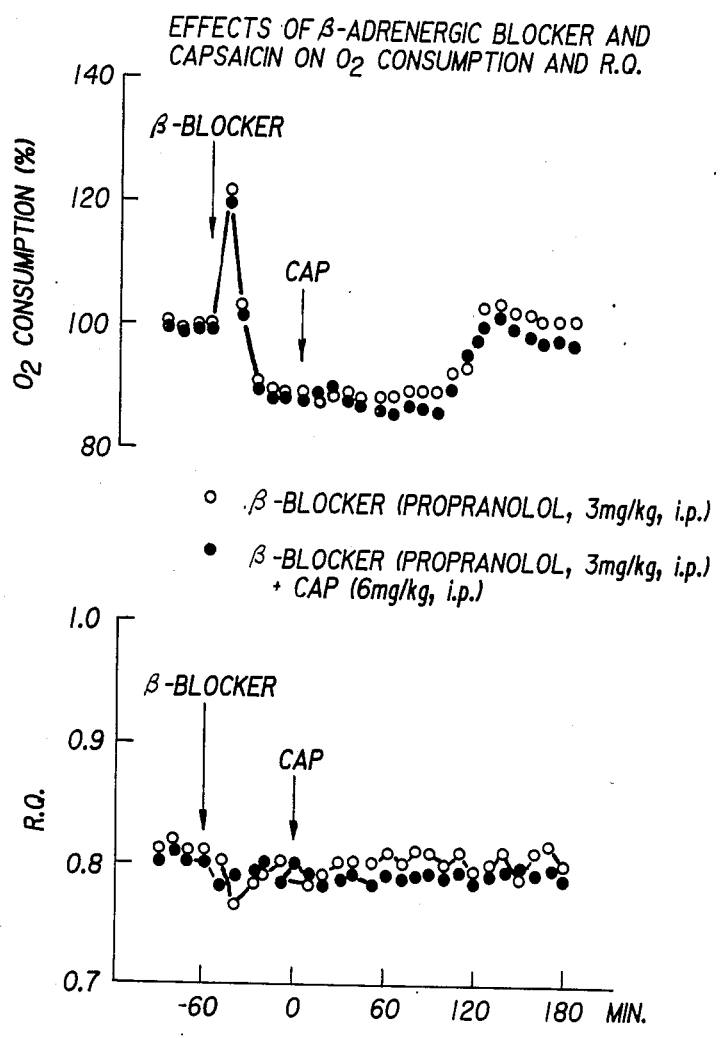
FIG. 9 shows the effects of CAP and adrenergic β-blocker upon oxygen consumption and the respiratory quotient.

A comparison with the changes in energy metabolism picture which Tanaka, et. al had established by using various types of hormones [Nourishment and Foodstuff, 31, No. 1, 1–7 (1978)] revealed that the data obtained above on capsaicin is very similar to the case when epinephrine (adrenaline) (FIG. 8) was used. To further characterize the mechanism of capsaicin's action, the compound was injected into rats previously treated with an adrenergic β-blocker. The result was that there was no change at all in the picture of energy metabolism as observed when capsaicin alone was injected. On the other hand, pretreatment with an adrenergic α-blocker or a ganglion blocker had no effect upon the changes in the picture of energy metabolism caused by injection of capsaicin. These results provide evidence that capsaicin accelerates energy metabolism through its direct or indirect adrenergic action, and that this action did help promote the lipid metabolism in the rats fed on highfat diets, leading to reduction in the amount of perirenal fat.

Similar lipid metabolism promoting action was also observed with vanillylamine. This suggests that the activity of the vanillylamides of the present invention may probably be ascribable to the action of vanillylamine formed by decomposition in living bodies.

EXAMPLE 1

Soybean oil containing each 0.28% of capsaicin, homocapsaicin or norcapsaisin was prepared by admixing each of 0.014 parts by weight of capsaicin, homocapsaicin or norcapsaicin with 5 parts by weight of soybean oil. Each of these soybean oils was given to 15 male Wister rats each having an initial weight of 170 to 180 grams at a daily dose of 0.5 g/head for ten days, together with a high-fat diet separately prepared (1 g casein, 4 g starch, 1 g sucrose, 3 g lard, 0.2 g mixed materials, 0.1 g mixed vitamins and 0.2 g cellulose per day).

A control group consisting of 15 male Wister rats each having an initial weight of 170 to 180 grams was fed on a commercial diet (Oriental Yeast Co., Ltd.; Oriental MF-Diet) for ten days so that the caloric intake was the same as in the test group. The average gain in body weight in the test group was 18.5 grams (18.5±6.1 grams) in contrast to 35.7 grams (35.7±6.3 grams) for the control group, which is a level approximately half that in the control group, even with the same caloric intake.

EXAMPLE 2

A mayonnaise containing 1% capsaicin was prepared by admixture of capsaicin-packed hard gelatin capsules which had been made by the usual method.

This capsaicin-containing mayonnaise was given to male Wister rats at a daily dose of 1 g/head for ten days, alternatively with a high-fat diet separately prepared (1 g casein, 4 g starch, 1 g sucrose, 2.5 g lard, 0.2 g mixed minerals, 0.1 g mixed vitamins and 0.2 g cellulose per day). A control group was fed on a commercial diet for ten days so that the caloric intake was the same as for the test group. The gain in body weight in the test group after ten days was approximately half that in the control group.

EXAMPLE 3

Several diets were prepared by mixing 10 parts by weight of casein, 40 parts by weight of starch, 10 parts by weight of sucrose, 2 parts by weight of mixed minerals, 1 parts by weight of mixed vitamins, 1 part by weight of cellulose and 0.014 part by weight of capsaicin, 0.014 part by weight of dihydrocapsaicin, 0.007 part by weight of vanillylamine, 0.009 part by weight of N-acetylvanillylamide, 0.019 part by weight of N-stearoylvanillylamide, 0.019 part by weight of N-linoleoylvanillylamide or 0.013 part by weight of 4-heptenoylvanillylamide.

Each of these diets was given to 15 male Wister rats each having an initial weight of 170 to 180 grams at a daily dose of 6.5 g/head for ten days, together with lard (3 g/day) and soybean oil (0.5 g/day).

A control group consisting 15 male Wister rats each having an initial weight of 170 to 180 grams was fed on a commercial diet (Oriental Yeast Co., Ltd.; Oriental MF-Diet) for ten days so that the caloric intake will be the same as in the test group. The average gain in body weight in the test group was 18.5 grams (18.5±6.1 grams) in contrast to 35.7 grams (35.7±6.3 grams) for the control group (a level approximately half that in the control group, even with the same caloric intake).

EXAMPLE 4

| Meat Tenderizer | |
|---|---|
| Commercial meat tenderizer ("Miola"; Ohtsuka Pharmaceutical Co., Ltd.) | 100 Parts |
| Capsaicin | 2 Parts |

Beef (fat content of 41%) was treated with a mixture of the above components so as to produce tenderized beef containing 0.01% of capsaicin. This treated beef was given to male Wister rats at a daily dose of 10 g/head for ten days, together with a commercial diet.

A control group was fed on the commercial diet alone for ten days so that the caloric intake was the same as that in the test group.

The gain in body weight in the test group was three fourths that in the control group, even with the same caloric intake.

EXAMPLE 5

| Sauce for Roast Meat | |
|---|---|
| Soy sauce (heavy grade) | 35.0 ml |
| Sweet sake (heavy grade) | 10.0 ml |
| Sweet sake (genuine) | 3.0 ml |
| Red wine | 3.0 ml |
| Sorbitol | 10.0 g |
| Sugar | 13.0 g |
| Sodium glutamate | 1.5 g |
| "AMIRICH CR"* | 0.5 g |
| "AJIEKIS B-1"** | 1.0 g |
| 50% Lactic acid | 0.3 g |
| Grated garlic | 4.5 g |
| Grated ginger | 1.5 g |
| Onion powder | 2.0 g |
| Capsaicin | 2.0 g |
| (or Homocapsaicin) | 2.0 g |
| (or Norcapsaicin) | 2.0 g |
| (or Dihydrocapsaicin) | 2.0 g |
| (or N—linoleoylvanillylamide) | 2.7 g |
| Pepper | 0.05 g |
| Sesame | 0.5 g |
| Water | 19.1 ml |

*,**Protein hydrolysate produced by Ajinomoto Co., Inc.

Sauces for roast meat were prepared by heating a mixture of the compositions listed above.

Beef (plate; fat content of 41.0% was soaked in each of these sauces, and each of the treated beeves was given to male Wister rats at a daily dose of 10 g/head for ten days, together with a commercial diet.

A control group was fed on the commercial diet alone for ten days so that the caloric intake was the same as that in the test group.

The gain in body weight in the test group was half that in the control group, even with the same caloric intake.

EXAMPLE 6

| Seasoning | | | |
|---|---|---|---|
| | Parts | Parts | Parts |
| Salt | 13.6 | 12.5 | 12.5 |
| Sugar | 83.0 | 80.7 | 80.7 |
| Capsaicin* | 3.4 | — | — |
| Dihydrocapsaicin* | — | 6.8 | — |
| N—linoleoylvanillylamide* | — | — | 9.2 |

*Encapsulated with hard gelatin by the usual method

Seasonings of the above compositions were emulsified with salad oil, yolk, vinegar and water so as to make dressings containing 1% capsaicin, dihydrocapsaicin or N-linoleoylvanillylamide.

Each of the dressings was given to male Wister rats at a daily dose of 1 g/head for ten days, alternately with a high-fat diet separately prepared (1 g casein, 4 g starch, 1 g sucrose, 2.5 g lard, 0.2 g mixed minerals, 0.1 mixed vitamins and 0.2 g cellulose per day).

A control group was fed on commercial diet for ten days so that the caloric intake was the same as that in the test group. The gain in body weight in the test group after ten days was approximately half that in the control group.

EXAMPLE 7

Diet formulations containing N-acetylvanillyl-amide, dihydrocapsaicin, N-stearoylvanillylamide, vanillylamine, bis-homocapsaicin, tris-homocapsaicin, N-linoleoylvanillylamide or 4-heptenoylvanillylamide were prepared as shown by the recipes listed in Tables 3 and 4.

The high-fat diets A through H prepared above, (fat energy ratio of 60%) were given to male Wister rats each having an initial weight of 170 to 180 grams at a daily dose of 6.5 g/head for ten days. At the same time, a control group was fed on a commercial diet (Oriental Yeast, Co., Ltd.; Oriental MF-Diet) for ten days. Measurements were made in each group of rats on the triglyceride levels in the blood, the weight of peri-renal adipose tissue, the activity of glucose-6-phosphate hydrogenase which participates in fatty acid synthesis in the liver, and the activity of lipoprotein lipase in the peri-renal adipose tissue. Significant reduction in the triglyceride level and in the weight of peri-renal adipose tissue was observed for the test groups fed on diets A through H which contained vanillylamine derivatives, when compared with the group fed on diet I, which contained no vanillylamine derivative. Significant increase in the activities of glucose-6-phosphate dehydrogenase and lipoprotein lipase was also noticed in the test groups fed on diets A through H. The results suggest that the diets of the present invention which contain a vanillylamine derivative help promote lipid metabolism in rats fed on high-fat foods.

TABLE 3

|  | High-fat Diet A | High-fat Diet B | High-fat Diet C | High-fat Diet D |
|---|---|---|---|---|
| Diet |  |  |  |  |
| Casein | 10% | 10% | 10% | 10% |
| Grain flour | 39 | 39.986 | 39 | 39 |
| Sucrose | 10 | 10 | 10 | 10 |
| Mixed minerals | 2 | 2 | 2 | 2 |
| Mixed vitamins | 1 | 1 | 1 | 1 |
| Cellulose | 2 | 2 | 2 | 2 |
| N—acetylvanillylamide | 0.009 | — | — | — |
| Dihydrocapsaicin | — | 0.014 | — | — |
| N—stearoylvanillylamide | — | — | 0.019 | — |
| Vanillylamine | — | — | — | 0.007 |
| Lard | 30 | 30 | 30 | 30 |
| Soybean oil | 5 | 5 | 5 | 5 |

TABLE 4

|  | High-fat Diet E | High-fat Diet F | High-fat Diet G | High-fat Diet H | High-fat Diet I |
|---|---|---|---|---|---|
| Diet |  |  |  |  |  |
| Casein | 10% | 10% | 10% | 10% | 10% |
| Grain flour | 39 | 39.986 | 39 | 39 | 39 |
| Sucrose | 10 | 10 | 10 | 10 | 10 |
| Mixed minerals | 2 | 2 | 2 | 2 | 2 |
| Mixed vitamines | 1 | 1 | 1 | 1 | 1 |
| Cellulose | 2 | 2 | 2 | 2 | 2 |
| Bis-Homocapsaicin | 0.015 | — | — | — | — |
| Tris-homocapsaicin | — | 0.016 | — | — | — |
| N—linoleoylvanillylamide | — | — | 0.019 | — | — |
| 4-Heptenoylvanillylamide | — | — | — | 0.013 | — |
| Lard | 30 | 30 | 30 | 30 | 30 |
| Soybean oil | 5 | 5 | 5 | 5 | 5 |

EXAMPLE 8

One part by weight of N-acetylvanillylamide was intimately mixed with 99 parts of butter. A sensory test proved that this mixture has the same taste and flavor as commercial butter, with no pungent taste detected.

This formulation was given to 15 male Wister rats each having an initial weight of 170 to 180 grams at a daily dose of 3.5 g/head for ten days, together with a high-fat diet separately prepared (1 g casein, 4 g starch, 1 g sucrose, 2.5 g lard, 0.2 g mixed minerals, 0.1 g mixed vitamins and 0.2 g cellulose per day).

At the same time a control group consisting 15 male Wister rats each having an initial weight of 170 to 180 grams was fed on a commercial diet (Oriental Yeast Co., Ltd.; Oriental MF-Diet) for ten days so that the caloric intake will be the same as in the test group.

The average gain in body weight in the test group was approximately half that in the control group, even with the same caloric intake.

Having now fully described this invention, it will be apparent to one of ordinary skill in the art that many changes and modifications can be made thereto without departing from the spirit or scope of the invention as set forth herein.

What is claimed as new and intended to be secured by Letters Patent is:

1. A method of accelerating lipid metabolism for reduction or prevention of accumulation of body fat in a subject, comprising:
   administering to said subject a lipid metabolism accelerating amount of a vanillylamine derivative selected from the group consisting of vanillylamine, a vanillylamide derived from an unsaturated carboxylic acid wherein said acid has from 8 to 18 carbon atoms, or a vanillylamide derived from a saturated carboxylic acid wherein said saturated carboxylic acid has from 2 to 22 carbon atoms, in a food substance.

2. The method of claim 1, wherein the lipid metabolism accelerating amount of said vanillylamine derivative in said food substance ranges from 0.01 to 1%.

3. The method of claim 2, wherein the amount of said vanillylamide derivative ranges from 0.1 to 1%.

4. The method of claim 1, wherein said food substance is an edible fat or fat containing food.

5. The method of claim 1, wherein said food substance contains no fat.

6. The method of claim 1, wherein said vanillylamide derivative is capsaicin.

7. The method of claim 1, wherein said vanillylamide derivative is norcapsaicin.

8. The method of claim 1, wherein said vanillylamide derivative is homocapsaicin.

9. The method of claim 4, wherein said edible fat is an animal fat, an animal oil or vegetable oil.

* * * * *